(12) United States Patent
Takasugi et al.

(10) Patent No.: US 9,026,398 B2
(45) Date of Patent: May 5, 2015

(54) MOTION ANALYSIS DEVICE AND MOTION ANALYSIS METHOD FOR ANALYZING DEFORMATION OF MEASUREMENT OBJECT

(75) Inventors: Toshiyasu Takasugi, Hadano (JP); Masatoshi Sato, Hashima (JP); Kazuo Nomura, Shiojiri (JP)

(73) Assignee: Seiko Epson Corporation (JP)

( * ) Notice: Subject to any disclaimer, the term of this patent is extended or adjusted under 35 U.S.C. 154(b) by 574 days.

(21) Appl. No.: 13/347,015

(22) Filed: Jan. 10, 2012

(65) Prior Publication Data

US 2012/0179418 A1 Jul. 12, 2012

(30) Foreign Application Priority Data

Jan. 11, 2011 (JP) ................................. 2011-003012

(51) Int. Cl.
*G06F 15/00* (2006.01)
*A63B 24/00* (2006.01)
*A63B 69/36* (2006.01)

(52) U.S. Cl.
CPC .............. *A63B 24/0003* (2013.01); *A63B 69/36* (2013.01); *A63B 69/3611* (2013.02); *A63B 2220/34* (2013.01); *A63B 2220/833* (2013.01); *A63B 2225/50* (2013.01); *A63B 2220/40* (2013.01)

(58) Field of Classification Search
CPC ........... A63B 69/3632; A63B 2220/16; A63B 24/0021; A63B 71/0622; A63B 2220/836; A63B 69/38; A63B 2024/0034; A63B 2069/0008; A63B 2220/40; A63B 2220/808; A63B 69/3623; A63B 24/0062; A63B 69/0095; A63B 2024/0031; A63B 2024/0068; A63B 2220/34; A63B 2220/64

USPC .......... 702/151; 473/407, 409, 221, 223, 224, 473/316, 376, 22, 269, 131
See application file for complete search history.

(56) References Cited

U.S. PATENT DOCUMENTS 7,297,070 B2 * 11/2007 Ashida et al. ................. 473/223
7,624,612 B2 * 12/2009 Toda et al. .................... 72/390.6
7,871,333 B1 * 1/2011 Davenport et al. ........... 473/223
(Continued)

FOREIGN PATENT DOCUMENTS

CA 2241359 A1 * 12/1999
CN 101031803 A 9/2007
(Continued)

*Primary Examiner* — Carol S Tsai
(74) *Attorney, Agent, or Firm* — Harness, Dickey & Pierce, P.L.C.

(57) ABSTRACT

A motion analysis device includes two posture angle sensors attached to a measurement object at locations distant from each other, a data acquisition section, a posture angle correction section, and a deformation amount calculation section. The data acquisition section acquires data of a first posture angle and a second posture angle respectively detected by the posture angle sensors. The posture angle correction section corrects a difference between the first posture angle and the second posture angle after starting a motion of the measurement object in accordance with a difference between the first posture angle and the second posture angle before starting the motion of the measurement object. The deformation amount calculation section calculates a deformation amount of the measurement object based on a difference between the first posture angle and the second posture angle corrected by the posture angle correction section.

10 Claims, 11 Drawing Sheets

(56) References Cited

U.S. PATENT DOCUMENTS

| | | | |
|---|---|---|---|
| 8,142,301 B2* | 3/2012 | Haag et al. | 473/222 |
| 8,210,960 B1* | 7/2012 | Davenport | 473/223 |
| 8,221,257 B2* | 7/2012 | Davenport | 473/223 |
| 8,306,657 B2* | 11/2012 | Yoshiike et al. | 700/246 |
| 8,475,300 B2* | 7/2013 | Ueda | 473/409 |
| 2004/0259651 A1* | 12/2004 | Storek | 473/131 |
| 2005/0215335 A1* | 9/2005 | Marquardt | 473/131 |
| 2005/0215340 A1* | 9/2005 | Stites et al. | 473/233 |
| 2006/0052173 A1* | 3/2006 | Telford | 473/131 |
| 2006/0211510 A1* | 9/2006 | Ashida et al. | 473/316 |
| 2008/0033679 A1 | 2/2008 | Yamada et al. | |
| 2009/0003861 A1* | 1/2009 | Motoyama | 399/51 |
| 2009/0247312 A1 | 10/2009 | Sato et al. | |
| 2010/0248837 A1* | 9/2010 | Suzuki et al. | 463/36 |
| 2012/0050529 A1* | 3/2012 | Bentley | 348/139 |
| 2012/0108351 A1* | 5/2012 | Tamura | 473/213 |

FOREIGN PATENT DOCUMENTS

| | | |
|---|---|---|
| CN | 101850172 A | 10/2010 |
| JP | 04-141186 | 5/1992 |
| JP | 2003-102886 | 4/2003 |
| JP | 2008-073210 | 4/2008 |
| JP | 2009-240677 | 10/2009 |

* cited by examiner

MOTION ANALYSIS DEVICE AND MOTION ANALYSIS METHOD FOR ANALYZING DEFORMATION OF MEASUREMENT OBJECT

BACKGROUND

1. Technical Field

The present invention relates to a motion analysis device and a motion analysis method.

2. Related Art

In the characteristic evaluation of a golf club, analysis of the deflection and the torsion thereof when making a swing is performed. In the past, there has been known a method of shooting the behavior of a golf club when making a swing with a camera, and then analyzing the deflection and the torsion of the golf club based on the shot image. However, since the image is analyzed in this method, there is a disadvantage that it is difficult to measure the deformation amount due to the deflection and the torsion with high accuracy, and further, it takes time from the measurement until the actual data is obtained.

On the other hand, in JP-A-2008-73210, there is proposed a method of attaching gyro sensors respectively to a head portion and a grip portion of a golf club to thereby evaluate the head speed of a swing, the carry, and so on, and it is possible to apply this method to the analysis of the deflection and the torsion of a golf club. Specifically, the deflection amount and the torsion amount of the golf club can be measured using the difference between the angular velocities detected by the two gyro sensors attached respectively to the head portion and the grip portion.

However, according to this method, since the error in the installation angle of the gyro sensor attached to the grip portion and the installation angle of the gyro sensor attached to the head portion causes the error in the detection sensitivity of the angular velocity, it is required to accurately conform the installation angles to each other. However, since the grip portion and the head portion are distant roughly 1 m from each other, it is extremely difficult to accurately conform the installation angles of the two gyro sensors to each other. If the error in the installation angle can be measured, it is possible to correct the angular velocities obtained from the gyro sensors. However, it is also extremely difficult to accurately measure the error in the installation angle. Therefore, in the case in which a high analysis accuracy is required, the method using the gyro sensors is applicable.

Such an analysis of the deformation amount due to the deflection or the torsion is performed in a variety of fields besides the golf club, and a new method realizing a high analysis accuracy has been required.

SUMMARY

An advantage of some of the aspects of the invention is to provide a motion analysis device and a motion analysis method capable of analyzing a deformation amount of a measurement object with high accuracy.

(1) An aspect of the invention is directed to a motion analysis device including a first posture angle sensor attached to a measurement object, and adapted to detect a first posture angle, a second posture angle sensor attached to the measurement object at a location distant from the first posture angle sensor, and adapted to detect a second posture angle, a data acquisition section adapted to acquire data of the first posture angle and the second posture angle, a posture angle correction section adapted to correct a difference between the first posture angle and the second posture angle after starting a motion of the measurement object in accordance with a difference between the first posture angle and the second posture angle before starting the motion of the measurement object, and a deformation amount calculation section adapted to calculate a deformation amount of the measurement object based on a difference between the first posture angle and the second posture angle corrected by the posture angle correction section.

Any object deformable in motion can be adopted as the measurement object. Further, a motion of the measurement object denotes a motion in which the measurement object changes at least one of the position and the posture, and includes the case in which the measurement object is provided with a motor, and voluntarily causes a motion, and the case in which a motion is caused by an external force applied to the measurement object.

The motion analysis device according to this aspect of the invention uses the fact that the difference is caused between the posture angles detected by two posture angle sensors in accordance with the error in the installation angles of the two posture angle sensors, measures the difference in the posture angle between the two points of the measurement object as an offset before the motion starts, and then calculates the difference in the posture angle between the two points after the motion starts with the offset correction. Thus, since the variation of the difference in the posture angle between the two points caused by the motion of the measurement object can accurately be calculated, the deformation amount between the two points can be analyzed with high accuracy.

(2) The motion analysis device of the aspect of the invention may be configured such that the posture angle correction section performs the correction by subtracting the difference between the first posture angle and the second posture angle before starting the motion of the measurement object from the difference between the first posture angle and the second posture angle after starting the motion of the measurement object.

(3) Another aspect of the invention is directed to a motion analysis device including a first posture angle sensor attached to a measurement object, and adapted to detect a first angular velocity and a first posture angle, a second posture angle sensor attached to the measurement object at a location distant from the first posture angle sensor, and adapted to detect a second angular velocity and a second posture angle, a data acquisition section adapted to acquire data of the first posture angle, the first angular velocity, the second posture angle, and the second angular velocity, an angular velocity correction section adapted to correct a difference between the first angular velocity and the second angular velocity in accordance with a difference between the first posture angle and the second posture angle, and a deformation amount calculation section adapted to calculate a deformation amount of the measurement object by integrating the difference between the first angular velocity and the second angular velocity corrected by the angular velocity correction section.

The motion analysis device according to this aspect of the invention uses the fact that the difference is caused between the posture angles detected by two posture angle sensors in accordance with the error in the installation angles of the two posture angle sensors, and corrects the difference in the angular velocity between the two points of the measurement object in accordance with the difference in the posture angle between the two points. Further, since the variation of the difference in the posture angle between the two points can accurately be calculated by integrating the difference between the angular velocities after the correction, the deformation amount between the two points can be analyzed with high accuracy.

(4) The motion analysis device of the aspect of the invention may be configured such that the angular velocity correction section corrects the difference between the first angular velocity and the second angular velocity by converting one of the first angular velocity and the second angular velocity into an angular velocity with respect to a detection axis of the other of the first angular velocity and the second angular velocity in accordance with the difference between the first posture angle and the second posture angle, and calculating a difference between the first angular velocity and the second angular velocity the one of which is converted.

(5) The motion analysis device of the aspect of the invention may be configured such that the measurement object is a golf club.

According to the motion analysis device of this configuration, since the variation of the difference in the posture angle between the two points caused by the swing of the golf club can accurately be calculated, the deformation amount of the golf club during the swing can be analyzed with high accuracy.

(6) The motion analysis device of the aspect of the invention may be configured such that the first posture angle sensor is attached to one of a grip section and a shaft section of the golf club, and the second posture angle sensor is attached to a head section of the golf club.

According to this configuration, the deflection amount of the shaft section of the golf club and the torsion amount of the head section can be analyzed with high accuracy.

(7) Yet another aspect of the invention is directed to a motion analysis method of a measurement object including: attaching a first posture angle sensor adapted to detect a first posture angle and a second posture angle sensor adapted to detect a second posture angle to the measurement object at locations distant from each other, acquiring data of the first posture angle and the second posture angle, correcting a difference between the first posture angle and the second posture angle after starting a motion of the measurement object in accordance with a difference between the first posture angle and the second posture angle before starting the motion of the measurement object, and calculating a deformation amount of the measurement object based on a difference between the first posture angle and the second posture angle corrected in the correcting.

The motion analysis method of this configuration uses the fact that the difference is caused between the posture angles detected by two posture angle sensors in accordance with the error in the installation angles of the two posture angle sensors, measures the difference in the posture angle between two points of the measurement object as an offset before the motion starts, and then calculates the difference in the posture angle between the two points after the motion starts with the offset correction. Thus, since the variation of the difference in the posture angle between the two points caused by the motion of the measurement object can accurately be calculated, the deformation amount between the two points can be analyzed with high accuracy.

(8) Still yet another aspect of the invention is directed to a motion analysis method of a measurement object including: attaching a first posture angle sensor adapted to detect a first angular velocity and a first posture angle and a second posture angle sensor adapted to detect a second angular velocity and a second posture angle to the measurement object at locations distant from each other, acquiring data of the first posture angle, the first angular velocity, the second posture angle, and the second angular velocity, correcting a difference between the first angular velocity and the second angular velocity in accordance with a difference between the first posture angle and the second posture angle, and calculating a deformation amount of the measurement object by integrating the difference between the first angular velocity and the second angular velocity corrected in the correcting.

The motion analysis method of this configuration uses the fact that the difference is caused between the posture angles detected by two posture angle sensors in accordance with the error in the installation angles of the two posture angle sensors, and corrects the difference in the angular velocity between the two points of the measurement object in accordance with the difference in the posture angle between the two points. Further, since the variation of the difference in the posture angle between the two points can accurately be calculated by integrating the difference between the angular velocities after the correction, the deformation amount between the two points can be analyzed with high accuracy.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail with reference to the accompanying drawings. It should be noted that the embodiments described below do not unreasonably limit the content of the invention as set forth in the appended claims. Further, all of the constituents described below are not necessarily essential elements of the invention.

1. First Embodiment

Figure 1:
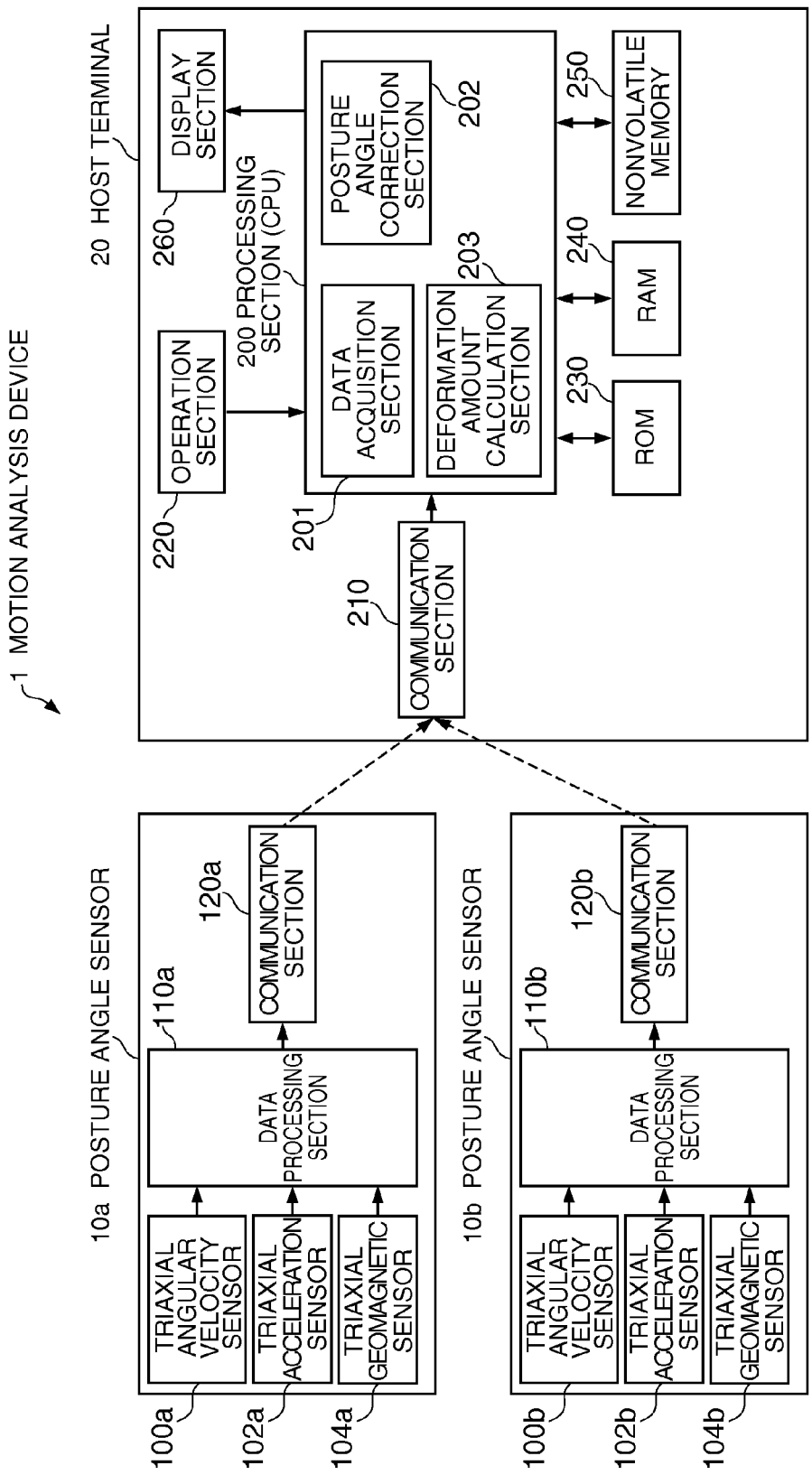
FIG. 1 is a diagram showing a configuration of a motion analysis device according to a first embodiment of the invention.

FIG. 1 is a diagram showing a configuration of a motion analysis device according to a first embodiment. The motion analysis device 1 according to the present embodiment is configured including two posture angle sensors 10a, 10b, and a host terminal 20. The posture angle sensors 10a, 10b and the host terminal 20 are connected to each other in a wired or wireless manner. The posture angle sensors 10a, 10b are attached to a measurement object to be the object of the motion analysis at respective locations distant from each other.

The posture angle sensor 10a includes, for example, a triaxial angular velocity sensor 100a, a triaxial acceleration sensor 102a, a triaxial geomagnetic sensor 104a, a data processing section 110a, and a communication section 120a.

The triaxial angular velocity sensor 100a detects the angular velocities around three axes (an $x_1$ axis, a $y_1$ axis, and a $z_1$ axis) perpendicular to each other, and then outputs a signal (triaxial angular velocity data) corresponding to the levels of the triaxial angular velocities thus detected.

The triaxial acceleration sensor 102a detects the acceleration in each of the three axial directions perpendicular to each other, and then outputs a signal (triaxial acceleration data) corresponding to the level of the triaxial acceleration thus detected.

The triaxial geomagnetic sensor 104a detects the geomagnetism in each of the three axial directions perpendicular to each other, and then outputs a signal (triaxial geomagnetic data) corresponding to the intensity of the triaxial geomagnetism thus detected.

It should be noted that the triaxial angular velocity sensor 100a, the triaxial acceleration sensor 102a, and the triaxial geomagnetic sensor 104a are attached so that the three axes of the sensors match each other. Alternatively, in the case in which the three axes of the triaxial angular velocity sensor 100a, the triaxial acceleration sensor 102a, and the triaxial geomagnetic sensor 104a do not match each other, and the error in the installation angles exists, the data processing section 110a converts, for example, the triaxial acceleration data output by the triaxial acceleration sensor 102a and the triaxial geomagnetic data output by the triaxial geomagnetic sensor 104a into the acceleration data and the geomagnetic data in the three axes (the $x_1$ axis, the $y_1$ axis, and the $z_1$ axis) directions of the triaxial angular velocity sensor 100a by the coordinate conversion using the correction parameter generated by the data processing section 111a and then stored in a storage section, not shown, in advance.

The data processing section 110a performs a process of calculating the posture angle of the posture angle sensor 10a in addition to the coordinate conversion process of the triaxial acceleration data and the triaxial geomagnetic data, if necessary. It is also possible to define, for example, an absolute coordinate system (an XYZ coordinate system) having a northern direction and an eastern direction in a horizontal plane as X and Y axes, and a vertically upward direction (the direction opposite to the direction of gravitational force) as a Z axis, and calculate the posture angles of the posture angle sensors 10a, 10b in the absolute coordinate system (the XYZ coordinate system). For example, it is possible to set the measurement object to a resting state, and identify the directions of the $x_1$ axis, the $y_1$ axis, and the $z_1$ axis in the XYZ coordinate system based on the gravitational direction obtained from the triaxial acceleration data and the northern direction obtained from the geomagnetic data to thereby calculate the posture angle (an initial posture angle) of the posture angle sensor 10a in an initial state (a resting state). Further, after the measurement object starts the motion, the posture angle of the posture sensor 10a in the XYZ coordinate system can be calculated using the triaxial angular velocity data. The posture angle can be expressed using, for example, rotational angles (a roll angle $\psi$, a pitch angle $\theta$, and a yaw angle $\phi$) around the X axis, the Y axis, and the Z axis, an Euler angle, and a quaternion.

Further, the data processing section 110a performs a process of outputting a packet formed by combining the posture angle data thus calculated with time information and so on to the communication section 120. The packet data can be arranged to include the triaxial angular velocity data, the triaxial acceleration data, the triaxial geomagnetic data, and so on besides the posture angle data. Further, the data processing section 110a can be arranged to perform processes of the bias correction and the temperature correction of the triaxial angular velocity sensor 100a, the triaxial acceleration sensor 102a, and the triaxial geomagnetic sensor 104a. It should be noted that it is possible to incorporate the functions of the bias correction and the temperature correction into the triaxial angular velocity sensor 100a, the triaxial acceleration sensor 102a, and the triaxial geomagnetic sensor 104a.

The communication section 120a performs a process of transmitting the packet data, which is received from the data processing section 110a, to the host terminal 20.

Similarly to the posture angle sensor 10a, the posture angle sensor 10b includes a triaxial angular velocity sensor 100b, a triaxial acceleration sensor 102b, a triaxial geomagnetic sensor 104b, a data processing section 110b, and a communication section 120b. Since the processes of the respective constituents thereof are the same as those in the posture angle sensor 10a, the explanation will be omitted.

The host terminal 20 is configured including a processing section (CPU) 200, a communication section 210, an operation section 220, a ROM 230, a RAM 240, a nonvolatile memory 250, and a display section 260. The host terminal 20 can be realized using a personal computer (PC) or a portable device such as a smartphone.

The communication section 210 performs a process of receiving the data transmitted from the posture angle sensors 10a, 10b, and then transmitting them to the processing section 200.

The operation section 220 performs a process of obtaining operation data from the user, and then transmitting it to the processing section 200. The operation section 220 corresponds to, for example, a touch panel display, a button, a key, and a microphone.

The ROM 230 stores a program for the processing section 200 to perform a variety of calculation processes and control processes, various programs and data for realizing application functions, and so on.

The RAM 240 is a storage section used as a working area of the processing section 200, and temporarily storing, for example, the program and data retrieved from the ROM 230, the data input from the operation section 220, and the calculation result obtained by the processing section 200 performing operations with the various programs.

The nonvolatile memory 250 is a recording section for storing the data required to be stored for a long period of time out of the data generated by the processing of the processing section 200.

The display section 260 is for displaying the processing result of the processing section 200 as letters, graphs, or other images. The display section 260 corresponds to, for example, a CRT, an LCD, a touch panel display, and a head-mount display (HMD). It should be noted that it is also possible to arrange that the functions of the operation section 220 and the display section 260 are realized by a single touch panel display.

The processing section 200 performs various calculation processes on the data received from the posture angle sensors 10a, 10b via the communication section 210, and various control processes (e.g., display control on the display section 260) in accordance with the programs stored in the ROM 240.

In particular, in the present embodiment, the processing section 200 functions as a data acquisition section 201, a posture angle correction section 202, and a deformation amount calculation section 203. It should be noted that it is also possible for the processing section 200 of the present embodiment to have a configuration in which some of the functions are eliminated.

The data acquisition section 201 performs a process of acquiring the output data (the posture angle data) of the posture angle sensors 10a, 10b, which is received vie the communication section 210, at a constant period $\Delta t$. The data thus acquired is stored in, for example, the RAM 240.

The posture angle correction section 202 performs a process of correcting the difference between the posture angle (a first posture angle) of the posture angle sensor 10a and the posture angle (a second posture angle) of the posture angle sensor 10b after the measurement object starts the motion in accordance with the difference between the posture angle of the posture angle sensor 10a and the posture angle of the posture angle sensor 10b before the measurement object starts the motion. For example, the posture angle correction section 202 can be arranged to perform the correction by subtracting the difference between the posture angle of the posture angle sensor 10a and the posture angle of the posture angle sensor 10b before the measurement object starts the motion from the difference between the posture angle of the posture angle sensor 10a and the posture angle of the posture angle sensor 10b after the measurement object starts the motion.

The deformation amount calculation section 203 performs a process of calculating the deformation amount of the measurement object based on the difference between the posture angle of the posture angle sensor 10a and the posture angle of the posture angle sensor 10b thus corrected by the posture angle correction section 202.

Figure 2:
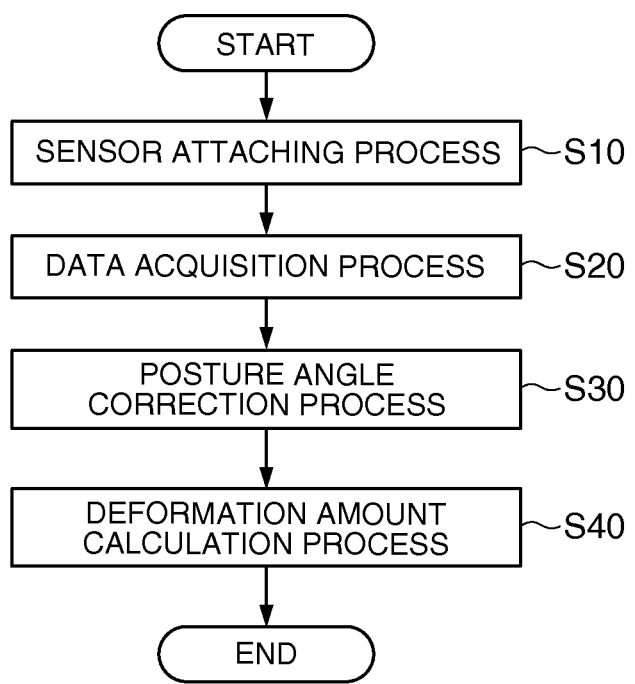
FIG. 2 is a flowchart showing an example of a method of calculating the deformation amount of a measurement object in the first embodiment.

FIG. 2 is a flowchart showing an example of a method of calculating the deformation amount of the measurement object using the motion analysis device according to the first embodiment.

Firstly, the posture angle sensors 10a, 10b are attached (S10, a sensor attaching process) to the measurement object at locations distant from each other.

Subsequently, the processing section 200 functions as the data acquisition section 201, and starts (S20, a data acquisition process) the process of continuously acquiring the respective posture angle data of the posture angle sensors 10a, 10b prior to the measurement object starting the motion.

Subsequently, the processing section 200 functions as the posture angle correction section 202, and corrects (S30, a posture angle correction process) the difference between the two posture angle data acquired in S20 after the measurement object starts the motion in accordance with the two posture angle data acquired in S20 before the measurement object starts the motion.

Finally, the processing section 200 functions as the deformation amount calculation section 203, and calculates (S40, a deformation amount calculation process) the deformation amount of the measurement object based on the difference between the two posture angle data thus corrected in S30.

Thus, the deformation amount of the measurement object can be calculated taking the initial state before the measurement object starts the motion as a reference (no deformation).

Specific Example

Then, the method according to the present embodiment will be explained citing an example of calculating the deformation amounts (a deflection amount and a torsion amount) of a golf club in a swing of the golf club. In this example, the golf club corresponds to the measurement object, the posture angle sensor 10a and the posture angle sensor 10b are attached to the golf club at the locations distant from each other, and the motion analysis device 1 functions as a golf swing analysis device. In particular, the posture angle correction section 202 performs a process of correcting the difference between the posture angle of the posture angle sensor 10a and the posture angle of the posture angle sensor 10b after a swing of the golf club is started in accordance with the difference between the posture angle of the posture angle sensor 10a and the posture angle of the posture angle sensor 10b before the swing of the golf club is started. Further, the deformation amount calculation section 203 performs a process of calculating the deformation amount of the golf club based on the difference between the posture angle of the posture angle sensor 10a and the posture angle of the posture angle sensor 10b thus corrected by the posture angle correction section 202.

Figure 3:
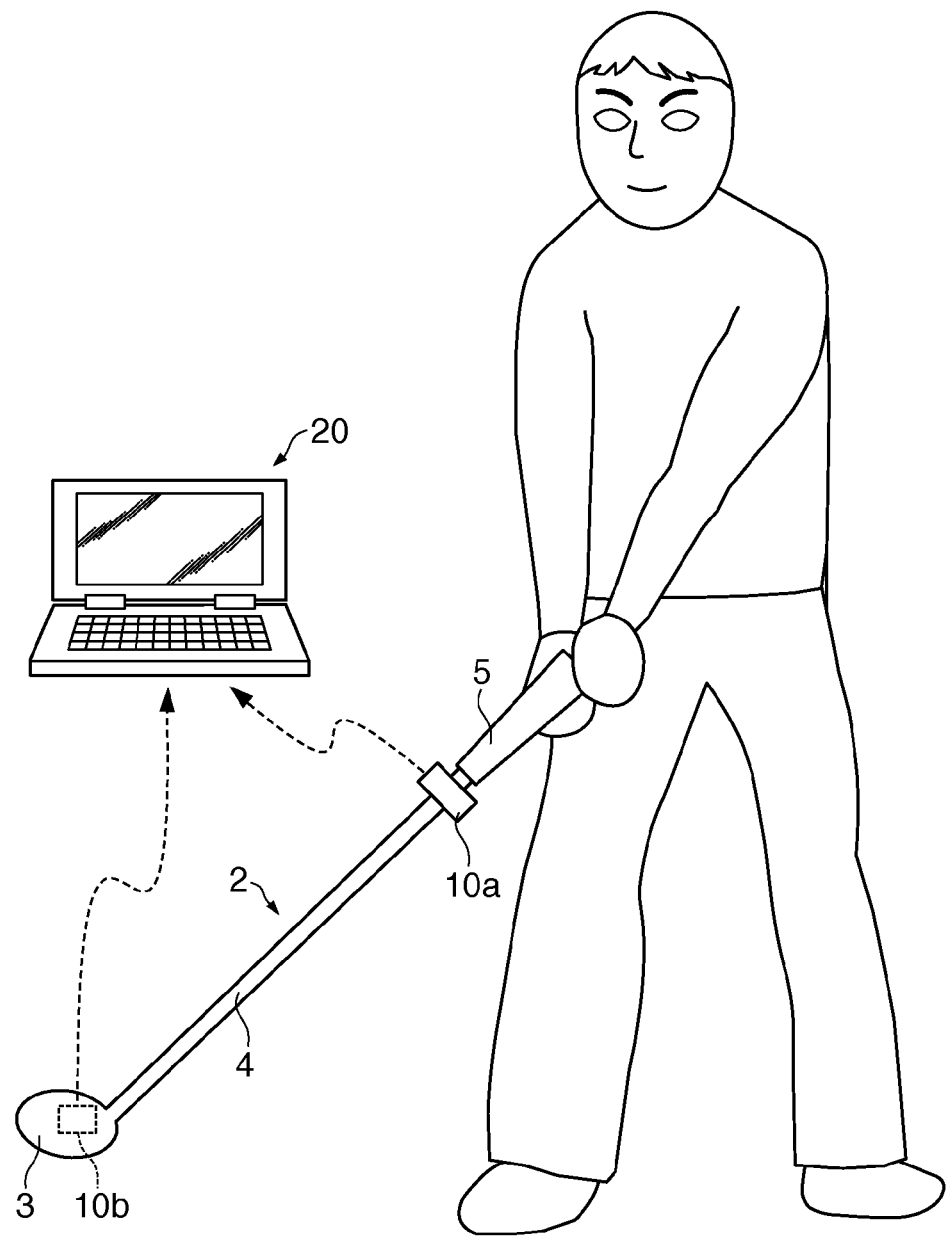
FIG. 3 is an explanatory diagram of a golf swing analysis device.

For example, as shown in FIG. 3, the posture angle sensor 10a is attached to a shaft section 4 of the golf club 2 at a position in the vicinity of the base thereof near to a grip section 5, and the posture angle sensor 10b is attached to a head section 3 of the golf club 2. The posture angle sensor 10a can be attached to the grip section 5, and the posture angle sensor 10b can be attached to the shaft section 4 at a position in the vicinity of the tip thereof near to the head section 3. The posture angle sensors 10a, 10b wirelessly transmit the respective posture angle data to the host terminal 20 (personal computer) at a constant period.

For example, after setting the golf club 2 in a resting state with an initial posture in which the long axis of the shaft section 4 conforms with the gravitational direction so as to minimize the deformation of the golf club 2, the subject grips the golf club 2, and makes a swing. The host terminal 20 acquires the respective posture angle data from the posture angle sensors 10a, 10b, corrects the difference between the two posture angles after the swing is started based on the difference between the two posture angles in the initial posture, and calculates the deformation amount of the golf club 2 due to the deflection of the shaft section 4 and the torsion of the head section 3.

Figure 4A:
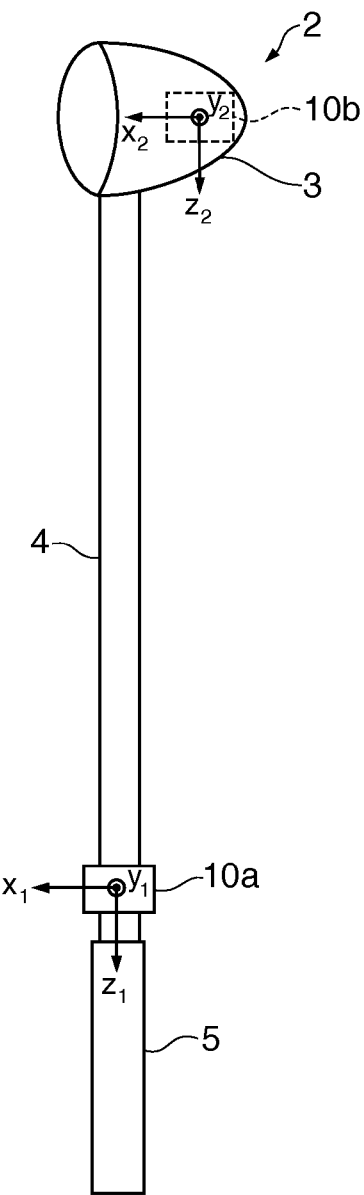
FIGS. 4A and 4B are diagrams showing an example of a shape of an initial posture of a golf club.
Figure 4B:
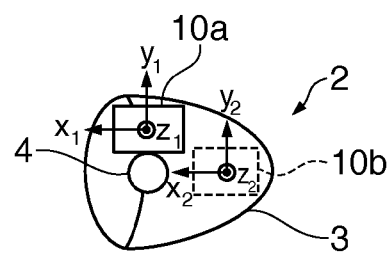
Figure 5A:
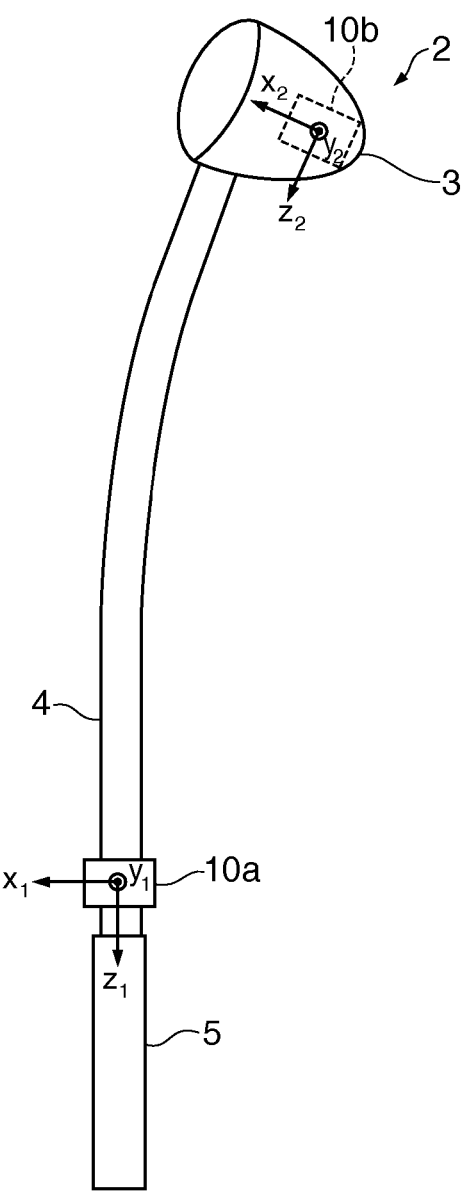
FIGS. 5A and 5B are diagrams showing an example of a shape of the golf club during a swing.
Figure 5B:
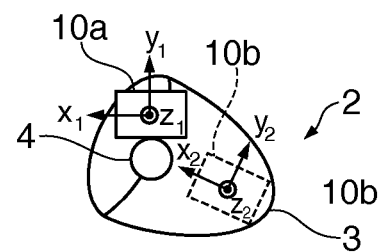

FIGS. 4A and 4B are diagrams showing an example of a shape of the initial posture of the golf club 2. In contrast, FIGS. 5A and 5B are diagrams showing an example of a shape of the golf club 2 during the swing. FIGS. 4A and 5A are diagrams showing a side of the golf club, and FIGS. 4B and 5B are diagrams of the golf club viewed from the grip side. It should be noted that in FIGS. 4B and 5B, the grip section 5 is omitted from the drawings.

As shown in FIGS. 4A and 4B, the posture angle sensor 10a is attached so that the $x_1$ axis is roughly perpendicular to the long axis direction of the shaft section 4 and roughly parallel to the swing direction, the $y_1$ axis is roughly perpendicular to the long axis direction of the shaft section 4 and roughly perpendicular to the swing direction, and the $z_1$ axis is roughly parallel to the long axis direction of the shaft section 4. Similarly, the posture angle sensor 10b is attached so that an $x_2$ axis is roughly perpendicular to the long axis direction of the shaft section 4 and roughly parallel to the swing direction, a $y_2$ axis is roughly perpendicular to the long axis direction of the shaft section 4 and roughly perpendicular to the swing direction, and a $z_2$ axis is roughly parallel to the long axis direction of the shaft section 4. In other words, in the initial posture, the $x_1$ axis, the $y_1$ axis, and the $z_1$ axis conform with the $x_2$ axis, the $y_2$ axis, and the $z_2$ axis, respectively, and the posture angle of the posture angle sensor 10a and the posture angle of the posture angle sensor 10b roughly conform with each other.

In contrast, during the swing, since the shaft section 4 deflects to a direction opposite to the swing direction, the $x_1$ axis and the $x_2$ axis are shifted from each other, and at the same time, the $z_1$ axis and the $z_2$ axis are shifted from each other as shown in FIG. 5A. Further, as shown in FIG. 5B, since the head section 3 is twisted around the long axis of the shaft section 4, the $x_1$ axis and the $x_2$ axis are shifted from each other, and at the same time, the $y_1$ axis and the $y_2$ axis are shifted from each other. In other words, during the swing, the posture angle of the posture angle sensor 10a and the posture angle of the posture angle sensor 10b fail to conform with each other. Therefore, in principle, the deformation amount of the golf club 2 can be calculated based on the difference between the posture angle of the posture angle sensor 10a and the posture angle of the posture angle sensor 10b during the swing. It can be said that the larger the difference is, the larger the deformation amount of the golf club 2 is.

Figure 6A:
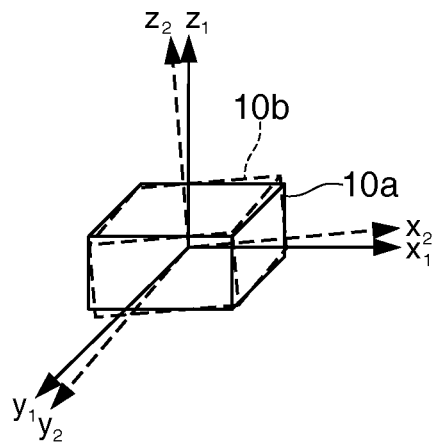
FIG. 6A is a diagram showing an example of the initial postures of two posture angle sensors.
Figure 6B:
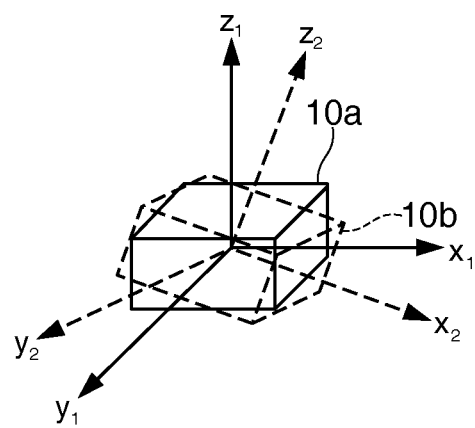
FIG. 6B is a diagram showing an example of the postures of the two posture angle sensors during a swing.

However, in reality, since there is an error in the installation angles of the posture angle sensors 10a, 10b, the posture angle of the posture angle sensor 10a and the posture angle of the posture angle sensor 10b fail to conform with each other in the initial posture. FIG. 6A is a diagram showing an example of the initial postures of the posture angle sensors 10a, 10b, and FIG. 6B is a diagram showing an example of the postures of the posture angle sensors 10a, 10b during the swing. In FIGS. 6A and 6B, the posture angle sensors 10a, 10b are illustrated with the respective centroids (origins) conformed with each other. As shown in FIG. 6A, in the initial posture, the $x_1$ axis, the $y_1$ axis, and the $z_1$ axis are slightly shifted from the $x_2$ axis, the $y_2$ axis, and the $z_2$ axis, respectively, due to the error in the installation angles. Therefore, as shown in FIG. 6B, although the $x_1$ axis, the $y_1$ axis, and the $z_1$ axis are more significantly shifted from the $x_2$ axis, the $y_2$ axis, and the $z_2$ axis during the swing due to the deflection of the shaft section 4 and the torsion of the head section 3, since an offset corresponding to the difference in the posture angle in the initial posture is caused, it is not achievable to accurately calculate the deformation amount of the golf club 2 only by the information of the difference in the posture angle during the swing.

Therefore, in the first embodiment, there is performed a correction calculation of subtracting the difference (the offset) between the posture angle of the posture angle sensor 10a and the posture angle of the posture angle sensor 10b in the initial posture from the difference between the posture angle of the posture angle sensor 10a and the posture angle of the posture angle sensor 10b during the swing. Then, the accurate deformation amount of the golf club 2 is calculated based on the difference in the posture angle after the correction.

Figure 7:
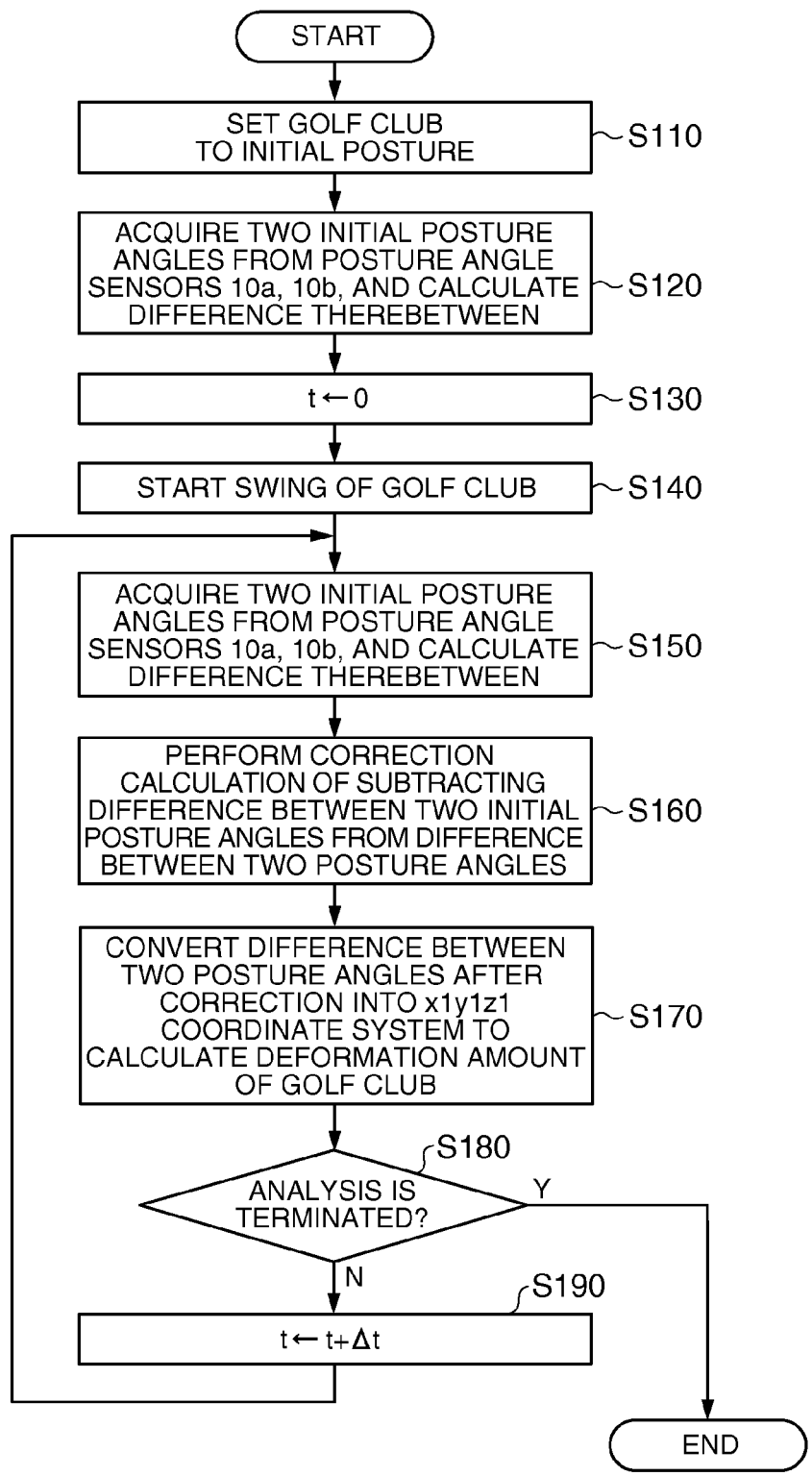
FIG. 7 is a flowchart showing an example of a calculation process of the deformation amount of a golf club in the first embodiment.

FIG. 7 shows an example of a flowchart of a calculation process of the deformation amount of the golf club 2 in the first embodiment.

Firstly, the subject sets (S110) the golf club to the initial posture, then the two initial posture angles are acquired from the posture angle sensors 10a, 10b, and then the difference therebetween is calculated (S120).

Then, the time t is reset (S130) to 0, and then the subject starts (S140) the swing of the golf club.

Then, the two posture angles are acquired from the posture angle sensors 10a, 10b, and then the difference therebetween is calculated (S150).

Then, the correction calculation of subtracting the difference between the two initial posture angles calculated in S120 from the difference between the two posture angles calculated in S150 is performed (S160).

Then, the difference (in the XYZ coordinate system) between the two posture angles after the correction obtained in S160 is converted into the $x_1y_1z_1$ coordinate system, and the deformation amount of the golf club is calculated (S170).

Figure 8A:
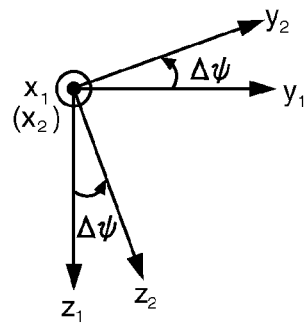
FIGS. 8A through 8C are explanatory diagrams of the difference between the posture angles of the two posture angle sensors.
Figure 8B:
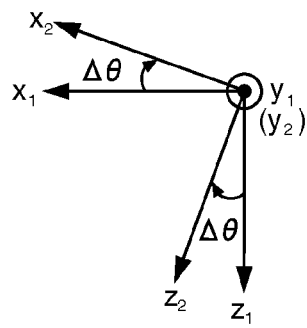
Figure 8C:
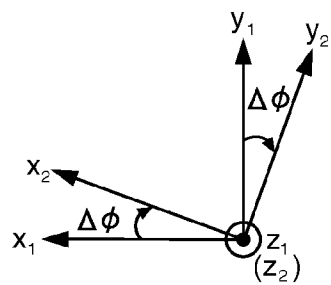

In the case of, for example, expressing the posture angle with the roll angle, the pitch angle, and the yaw angle, the difference between the two posture angles after the correction, which is converted into the $x_1y_1z_1$ coordinate system, is represented by the roll angle $\Delta\psi$ (the rotational angle around the $x_1$ axis), the pitch angle $\Delta\theta$ (the rotational angle around the $y_1$ axis), and the yaw angle $\Delta\phi$ (the rotational angle around the $z_1$ axis) as shown in FIG. 8A, FIG. 8B and FIG. 8C. Specifically, the roll angle $\Delta\psi$ corresponds to the deformation amount (mainly the torsion amount of the head section 3) of the golf club 2 on the $y_1z_1$ plane, the pitch angle $\Delta\theta$ corresponds to the deformation amount (mainly the deflection amount of the shaft section 4) of the golf club 2 on the $z_1x_1$ plane, and the yaw angle $\Delta\phi$ corresponds to the deformation amount (mainly the deflection amount of the head section 3) of the golf club 2 on the $x_1y_1$ plane. In the case of expressing the posture angle with an Euler angle or a quaternion, the roll angle $\Delta\psi$, the pitch angle $\Delta\theta$, and the yaw angle $\Delta\phi$ can be calculated by performing a known appropriate calculation.

Then, if the analysis is not terminated (N in S180), the time t is increased (S190) by $\Delta t$, and then the processes corresponding to S150 through 5170 are performed again.

The motion analysis device according to the first embodiment described hereinabove uses the fact that the difference between the posture angles detected by the posture angle sensors 10a, 10b occurs in accordance with the error in the installation angles of the posture angle sensors 10a, 10b, measures the difference in the posture angle between two points of the measurement object before the motion starts as an offset, and then calculates the difference in the posture angle between the two points after the motion starts with the offset correction. Thus, since the variation of the difference in the posture angle between the two points caused by the motion of the measurement object can accurately be calculated, the deformation amount between the two points can be analyzed with high accuracy.

Further, since the deformation amount of the measurement object can be calculated irrespective of the error in the installation angles of the posture angle sensors 10a, 10b, it is possible to attach the posture angle sensors 10a, 10b independently from each other to the measurement object at arbitrary positions and arbitrary angles. Therefore, according to the present embodiment, the motion analysis device easy to set and easy to deal with can be provided.

2. Second Embodiment

Figure 9:
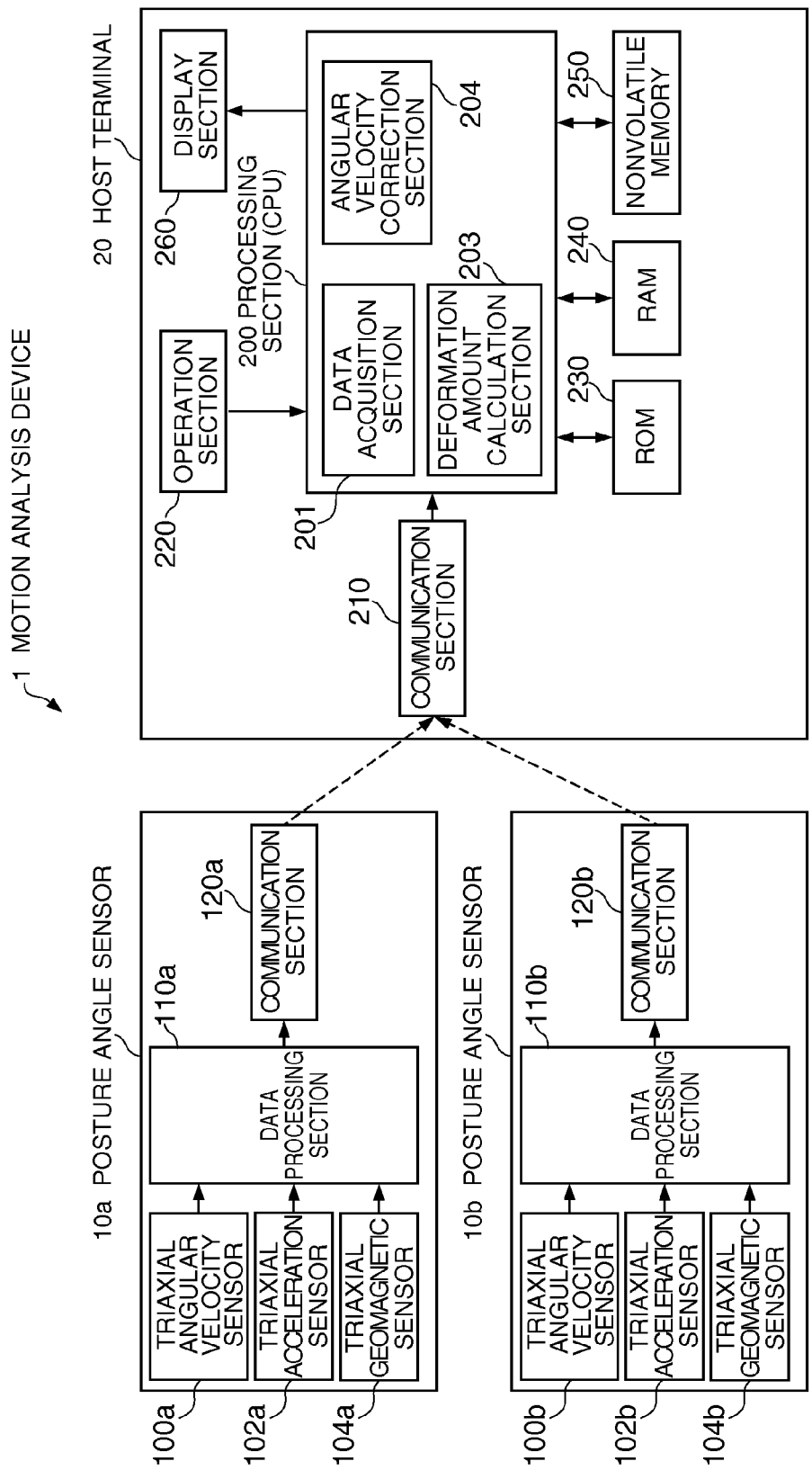
FIG. 9 is a diagram showing a configuration of a motion analysis device according to a second embodiment of the invention.

FIG. 9 is a diagram showing a configuration of a motion analysis device according to a second embodiment. In the motion analysis device according to the second embodiment, the posture angle sensor 10a transmits the angular velocity data ($\omega_{x1}$, $\omega_{y1}$, $\omega_{z1}$) around the three axes, namely the $x_1$ axis, the $y_1$ axis, and the $z_1$ axis, to the host terminal 20 at a constant period in addition to the posture angle data in the XYZ coordinate system. Further, the posture angle sensor 10b also transmits the angular velocity data ($\omega_{x2}$, $\omega_{y2}$, $\omega_{z2}$) around the three axes, namely the $x_2$ axis, the $y_2$ axis, and the $z_2$ axis, to the host terminal 20 at a constant period in addition to the posture angle data in the XYZ coordinate system. It should be noted that the posture angle sensors 10a, 10b are not necessarily required to output the angular velocity data around the three axes, but are required to output the angular velocity data around the axes necessary for the analysis.

Further, in the second embodiment, the processing section 200 functions as the data acquisition section 201, an angular velocity correction section 204, and the deformation amount calculation section 203. It should be noted that it is also possible for the processing section 200 of the present embodiment to have a configuration in which some of the functions are eliminated.

The data acquisition section 201 performs a process of acquiring the respective posture angle data and the triaxial angular velocity data from the posture angle sensors 10a, 10b at a constant period Δt.

The angular velocity correction section 204 performs a process of correcting the difference between the angular velocity (a first angular velocity) from the posture angle sensor 10a and the angular velocity (a second angular velocity) from the posture angle sensor 10b in accordance with the difference between the posture angle (the first posture angle) of the posture angle sensor 10a and the posture angle (the second posture angle) of the posture angle sensor 10b. For example, it is possible for the angular velocity correction section 204 to perform the process of correcting the difference between the angular velocities by converting one of the angular velocity from the posture angle sensor 10a and the angular velocity from the posture angle sensor 10b into the angular velocity with respect to the detection axis of the other of the angular velocities in accordance with the difference between the posture angle of the posture angle sensor 10a and the posture angle of the posture angle sensor 10b, and then calculating the difference between the two angular velocities after the conversion.

The deformation amount calculation section 203 performs the process of calculating the deformation amount of the measurement object by integrating the difference between the two angular velocities thus corrected by the angular velocity correction section 204.

The other constituents shown in FIG. 9 are the same as shown in FIG. 1, and are therefore denoted by the same reference symbols, and the explanation therefor will be omitted.

Figure 10:
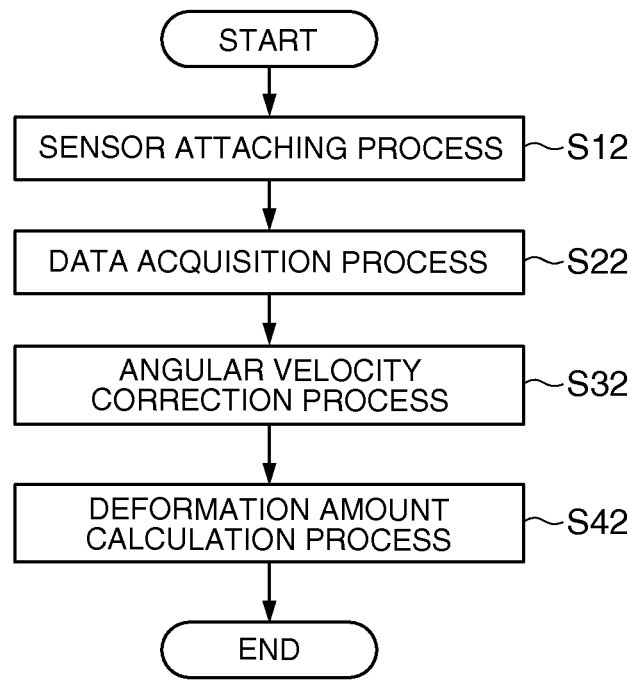
FIG. 10 is a flowchart showing an example of a method of calculating the deformation amount of a measurement object in the second embodiment.

FIG. 10 is a flowchart showing an example of a method of calculating the deformation amount of the measurement object in motion using the motion analysis device according to the second embodiment.

Firstly, the posture angle sensors 10a, 10b are attached (S12, a sensor attaching process) to the measurement object at locations distant from each other.

Subsequently, the processing section 200 functions as the data acquisition section 201, and starts (S22, a data acquisition process) the process of continuously acquiring the posture angle data and the angular velocity data from the posture angle sensors 10a, 10b prior to the measurement object starting the motion.

Subsequently, the processing section 200 functions as the angular velocity correction section 204, and corrects (S32, an angular velocity correction process) the difference between the two angular velocities acquired in S22 in accordance with the difference between the two posture angles acquired in S22.

Finally, the processing section 200 functions as the deformation amount calculation section 203, and calculates (S42, a deformation amount calculation process) the deformation amount of the measurement object by integrating the difference between the two angular velocities thus corrected in S32.

Specific Example

Then, the method according to the second embodiment will be explained citing an example of calculating the deformation amounts (a deflection amount and a torsion amount) of a golf club in a swing of the golf club similarly to the first embodiment. Similarly to the case explained in the first embodiment, also in this example, the golf club corresponds to the measurement object, the posture angle sensor 10a and the posture angle sensor 10b are attached to the golf club at the locations distant from each other, and the motion analysis device 1 functions as a golf swing analysis device.

In particular, the angular velocity correction section 204 calculates the difference in the posture angle between the posture angle sensors 10a, 10b every period Δt, and corrects (converts) the triaxial angular velocities $\omega_{x2}$, $\omega_{y2}$, and $\omega_{z2}$ acquired from the posture angle sensor 10b respectively to the angular velocities $\omega_{x2}'$, $\omega_{y2}'$, and $\omega_{z2}'$ around the three axes, namely the $x_1$ axis, the $y_1$ axis, and the $z_1$ axis after starting the swing of the golf club in accordance with the calculation result. For example, at time t, the angle $\Delta\psi_E(t)$ formed between the $x_1$ axis and the $x_2$ axis, the angle $\Delta\theta_E(t)$ formed between the $y_1$ axis and the $y_2$ axis, and the angle $\Delta\phi_E(t)$ formed between the $z_1$ axis and the $z_2$ axis are calculated from the posture angle difference of the posture angle sensors 10a, 10b, and the angular velocities $\omega_{x2}(t)$, $\omega_{y2}(t)$, and $\omega_{z2}(t)$ are corrected to the angular velocities $\omega_{x2}'(t)$, $\omega_{y2}'(t)$, and $\omega_{z2}'(t)$ using the formulas 1, 2, and 3 below, respectively $$\omega_{x2}'(t) = \frac{\omega_{x2}(t)}{\cos\Delta\psi_E(t)} \tag{1}$$

$$\omega_{y2}'(t) = \frac{\omega_{y2}(t)}{\cos\Delta\theta_E(t)} \tag{2}$$

$$\omega_{z2}'(t) = \frac{\omega_{z2}(t)}{\cos\Delta\phi_E(t)} \tag{3}$$

Further, in theory, the integral value $\Delta\psi(T)$ of the difference between the angular velocities $\omega_{x1}$, $\omega_{x2}'$ from the time t=0 to the time t=T, the integral value $\Delta\theta(T)$ of the difference between the angular velocities $\omega_{y1}$, $\omega_{y2}'$ from the time t=0 to the time t=T, and the integral value $\Delta\phi(T)$ of the difference between the angular velocities $\omega_{z1}$, $\omega_{z2}'$ from the time t=0 to the time t=T can be calculated using the formulas 4, 5, and 6 below, respectively.

$$\Delta\psi(T)=\int_0^T \{\omega_{x1}(t)-\omega_{x2}'(t)\}dt \tag{4}$$

$$\Delta\theta(T)=\int_0^T \{\omega_{y1}(t)-\omega_{y2}'(t)\}dt \tag{5}$$

$$\Delta\phi(T)=\int_0^T \{\omega_{z1}(t)-\omega_{z2}'(t)\}dt \tag{6}$$

These integral values $\Delta\psi(T)$, $\Delta\theta(T)$, and $\Delta\phi(T)$ correspond to the values $\Delta\psi$, $\Delta\theta$, and $\Delta\phi$ shown in FIGS. 8A, 8B, and 8C, respectively. Therefore, by calculating the integral values $\Delta\psi(T)$, $\Delta\theta(T)$, and $\Delta\phi(T)$, the deformation amount of the golf club 2 can be obtained.

It should be noted that in the practical process, the discrete integration of calculating $\Delta\psi(t+\Delta t)$, $\Delta\theta(t+\Delta t)$, and $\Delta\phi(t+\Delta t)$ by adding $\omega_{x1}(t)-\omega_{x2}'(t)$, $\omega_{y1}(t)-\omega_{y2}'(t)$, and $\omega_{z1}(t)-\omega_{z2}'(t)$ to $\Delta\psi(t)$, $\Delta\theta(t)$, and $\Delta\phi(t)$, respectively, is repeatedly performed until t+Δt=T is reached. Thus, the integral values $\Delta\psi(T)$, $\Delta\theta(T)$, and $\Delta\phi(T)$ are approximated. By setting Δt to a small value, the accuracy of approximation can be enhanced.

Figure 11:
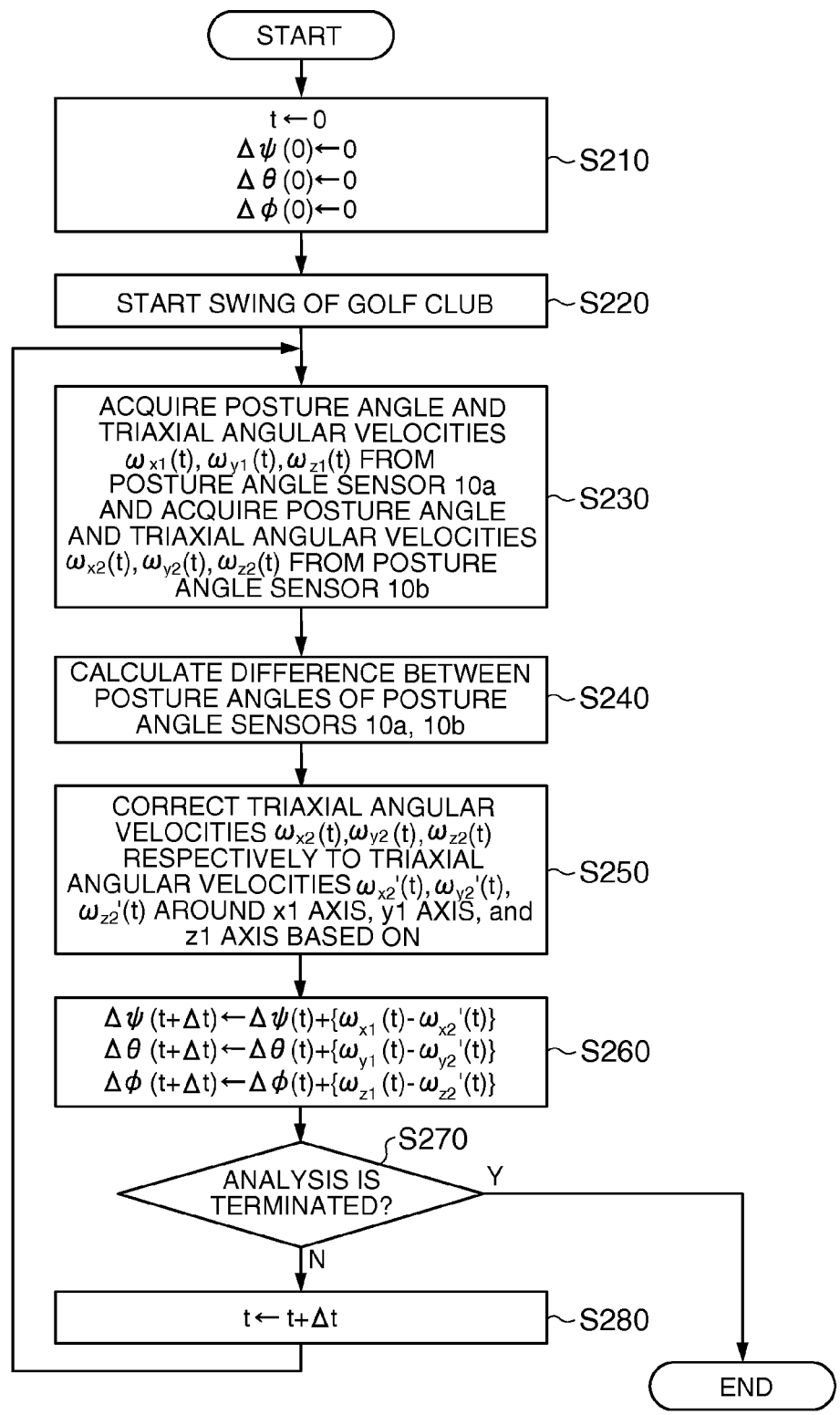
FIG. 11 is a flowchart showing an example of a calculation process of the deformation amount of a golf club in the second embodiment.

FIG. 11 shows an example of a flowchart of a calculation process of the deformation amount of the golf club 2 in the second embodiment.

Firstly, the time t, and the integral values $\Delta\psi(0)$, $\Delta\theta(0)$, and $\Delta\phi(0)$ are reset (S210) to 0, and then the subject starts (S220) the swing of the golf club.

Subsequently, the posture angle and the triaxial angular velocities $\omega_{x1}$, $\omega_{y1}$, and $\omega_{z1}$ are acquired (S230) from the posture angle sensor 10a, and at the same time, the posture angle and the triaxial angular velocities $\omega_{x2}$, $\omega_{y2}$, and $\omega_{z2}$ are acquired (S230) from the posture angle sensor 10b.

Then, the difference between the posture angle of the posture angle sensor 10a acquired in S230 and the posture angle of the posture angle sensor 10b acquired in S230 is calculated (S240).

Subsequently, based on the difference between the two posture angles calculated in S240, the triaxial angular velocities $\omega_{x2}(t)$, $\omega_{y2}(t)$, and $\omega_{z2}(t)$ are corrected (S250) to the triaxial angular velocities $\omega_{x2}'(t)$, $\omega_{y2}'(t)$, and $\omega_{z2}'(t)$ around the $x_1$ axis, the $y_1$ axis, and the $z_1$ axis, respectively.

Subsequently, $\{\omega_{x1}(t) - \omega_{x2}'(t)\}$ is added to $\Delta\psi(t)$ and is then substituted in $\Delta\psi(t+\Delta t)$, $\{\omega_{y1}(t) - \omega_{y2}'(t)\}$ is added to $\Delta\theta(t)$ and is then substituted in $\Delta\theta(t+\Delta t)$, and $\{\omega_{z1}(t) - \omega_{z2}'(t)\}$ is added to $\Delta\phi(t)$ and is then substituted (S260) in $\Delta\phi(t+\Delta t)$.

Then, if the analysis is not terminated (N in S270), the time t is increased (S280) by $\Delta t$, and then the processes corresponding to S230 through S260 are performed again.

The values $\Delta\psi(t)$, $\Delta\theta(t)$, and $\Delta\phi(t)$ thus obtained correspond respectively to the deformation amount of the golf club 2 on the $y_1z_1$ plane at the time t, the deformation amount thereof on the $z_1x_1$ plane, and the deformation amount thereof on the $x_1y_1$ plane.

The motion analysis device according to the second embodiment described hereinabove uses the fact that the difference between the posture angles detected by the posture angle sensors 10a, 10b occurs in accordance with the error in the installation angles of the posture angle sensors 10a, 10b, and corrects the difference in the angular velocity between two points of the measurement object before the motion starts in accordance with the difference in the posture angle between the two points. Further, since the variation of the difference in the posture angle between the two points can accurately be calculated by integrating the difference between the angular velocities after the correction, the deformation amount between the two points can be analyzed with high accuracy.

Further, since the deformation amount of the measurement object can be calculated irrespective of the error in the installation angles of the posture angle sensors 10a, 10b, it is possible to attach the posture angle sensors 10a, 10b independently from each other to the measurement object at arbitrary positions and arbitrary angles. Therefore, according to the present embodiment, the motion analysis device easy to set and easy to deal with can be provided.

The invention is not limited to the embodiments described above, but can be put into practice with various modifications within the scope or the spirit of the invention.

For example, although in the present embodiment the calculation process of the deformation amount of the measurement object is performed in real time, it is not necessarily required to perform the calculation process of the deformation amount of the measurement object in real time. It is also possible to arrange, for example, that the posture angle sensors 10a, 10b and the host terminal 20 are each provided with a memory card interface section instead of connecting the posture angle sensors 10a, 10b and the host terminal 20 to each other in a wireless or wired manner, and the posture angle sensors 10a, 10b write the posture angle data and so on in the memory card, and then the host terminal 20 reads out the data from the memory card to perform the calculation process of the deformation amount of the measurement object.

Further, although in the first embodiment, the processing section 200 (the data acquisition section 201) continuously acquires the posture angle data at a constant period and then calculates the deformation amount of the measurement object every time, if, for example, it is attempted to analyze only the deformation amount of the golf club at the maximum speed of the swing of the golf club, it is also possible to arrange that only the posture angle data in the initial posture and the posture angle data at the analysis timing are acquired, and then the deformation amount at the analysis timing is calculated.

Further, although in the embodiments described above the explanation is presented citing the example of attaching the two posture angle sensors to the measurement object and then calculating the deformation amount between the two points, it is also possible to arrange that three or more posture angle sensors are attached to the measurement object at locations distant from each other, and the deformation amount between any two of the points is calculated. According to this configuration, the deformation of the measurement object can more accurately be analyzed.

Further, although in the embodiments described above the explanation is presented citing the swing analysis of the golf club as an example, the invention can also be applied to a swing analysis of other exercise equipment, and further various applications such as an analysis of the deformation amount of a vehicle by attaching the posture angle sensors to the front, back, right, and left of the vehicle, or an analysis of the deformation amount of a tall building by attaching the posture angle sensor to a plurality of floors of the tall building.

The invention includes configurations (e.g., configurations having the same function, the same way, and the same result, or configurations having the same object and the same advantages) substantially the same as those described in the embodiment section. Further, the invention includes configurations obtained by replacing a non-essential part of the configurations described in the embodiment section. Further, the invention includes configurations exerting the same advantages or configurations capable of achieving the same object as the configurations described in the embodiment section. Further, the invention includes configurations obtained by adding technologies known to the public to the configurations described in the embodiment section.

The entire disclosure of Japanese Patent Application No. 2011-003012, filed Jan. 11, 2011 is expressly incorporated by reference herein.

What is claimed is:

1. A motion analysis device comprising:
    a first posture angle sensor attached to a measurement object, and adapted to detect a first posture angle;
    a second posture angle sensor attached to the measurement object at a location distant from the first posture angle sensor, and adapted to detect a second posture angle;
    a data acquisition section adapted to acquire data of the first posture angle and the second posture angle;
    a posture angle correction section adapted to correct a difference between the first posture angle and the second posture angle after starting a motion of the measurement object in accordance with a difference between the first posture angle and the second posture angle before starting the motion of the measurement object; and a deformation amount calculation section adapted to calculate a deformation amount of the measurement object based on a difference between the first posture angle and the second posture angle corrected by the posture angle correction section.

2. The motion analysis device according to claim 1, wherein
the posture angle correction section performs the correction by subtracting the difference between the first posture angle and the second posture angle before starting the motion of the measurement object from the difference between the first posture angle and the second posture angle after starting the motion of the measurement object.

3. A motion analysis device comprising:
a first posture angle sensor attached to a measurement object, and adapted to detect a first angular velocity and a first posture angle;
a second posture angle sensor attached to the measurement object at a location distant from the first posture angle sensor, and adapted to detect a second angular velocity and a second posture angle;
a data acquisition section adapted to acquire data of the first posture angle, the first angular velocity, the second posture angle, and the second angular velocity;
an angular velocity correction section adapted to correct a difference between the first angular velocity and the second angular velocity in accordance with a difference between the first posture angle and the second posture angle; and
a deformation amount calculation section adapted to calculate a deformation amount of the measurement object by integrating the difference between the first angular velocity and the second angular velocity corrected by the angular velocity correction section.

4. The motion analysis device according to claim 3, wherein
the angular velocity correction section corrects the difference between the first angular velocity and the second angular velocity by converting one of the first angular velocity and the second angular velocity into an angular velocity with respect to a detection axis of the other of the first angular velocity and the second angular velocity in accordance with the difference between the first posture angle and the second posture angle, and calculating a difference between the first angular velocity and the second angular velocity the one of which is converted.

5. The motion analysis device according to claim 1, wherein
the measurement object is a golf club.

6. The motion analysis device according to claim 3, wherein
the measurement object is a golf club.

7. The motion analysis device according to claim 5, wherein
the first posture angle sensor is attached to one of a grip section and a shaft section of the golf club, and
the second posture angle sensor is attached to a head section of the golf club.

8. The motion analysis device according to claim 6, wherein
the first posture angle sensor is attached to one of a grip section and a shaft section of the golf club, and
the second posture angle sensor is attached to a head section of the golf club.

9. A motion analysis method of a measurement object, comprising:
attaching a first posture angle sensor adapted to detect a first posture angle and a second posture angle sensor adapted to detect a second posture angle to the measurement object at locations distant from each other;
acquiring data of the first posture angle and the second posture angle;
correcting a difference between the first posture angle and the second posture angle after starting a motion of the measurement object in accordance with a difference between the first posture angle and the second posture angle before starting the motion of the measurement object; and
calculating a deformation amount of the measurement object based on a difference between the first posture angle and the second posture angle corrected in the correcting.

10. A motion analysis method of a measurement object, comprising:
attaching a first posture angle sensor adapted to detect a first angular velocity and a first posture angle and a second posture angle sensor adapted to detect a second angular velocity and a second posture angle to the measurement object at locations distant from each other;
acquiring data of the first posture angle, the first angular velocity, the second posture angle, and the second angular velocity;
correcting a difference between the first angular velocity and the second angular velocity in accordance with a difference between the first posture angle and the second posture angle; and
calculating a deformation amount of the measurement object by integrating the difference between the first angular velocity and the second angular velocity corrected in the correcting.

* * * * *